(12) United States Patent
Cheng et al.

(10) Patent No.: US 9,238,082 B2
(45) Date of Patent: Jan. 19, 2016

(54) METHOD OF BONDING GOLD NANOPARTICLES WITH DIETHYLENETRIAMINE PENTAACETIC ACID

(71) Applicant: Institute of Nuclear Energy Research, Atomic Energy Council, Executive Yuan, R.O.C., Taoyuan County (TW)

(72) Inventors: Chun-Chia Cheng, Taoyuan County (TW); Shiau-Shiun Guan, Taoyuan County (TW)

(73) Assignee: INSTITUTE OF NUCLEAR ENERGY RESEARCH, ATOMIC ENERGY COUNCIL, Executive Yuan, R.O.C., Lungtan, Taoyuan (TW)

( * ) Notice: Subject to any disclaimer, the term of this patent is extended or adjusted under 35 U.S.C. 154(b) by 347 days.

(21) Appl. No.: 13/965,328

(22) Filed: Aug. 13, 2013

(65) Prior Publication Data

US 2015/0051375 A1    Feb. 19, 2015

(51) Int. Cl.
*A61K 49/18* (2006.01)
*C07K 14/00* (2006.01)
*A61K 49/00* (2006.01)
*B82Y 5/00* (2011.01)

(52) U.S. Cl.
CPC .............. *A61K 49/0002* (2013.01); *B82Y 5/00* (2013.01); *Y10S 534/00* (2013.01)

(58) Field of Classification Search
None
See application file for complete search history.

(56) References Cited

PUBLICATIONS

Colloidal gold, Wikipedia article downloaded Sep. 21, 2015; 14 pages.*
Sherry et al.,"Stability constants for Gd+3 binding to model DTPA-conjugates and DTPA-proteins: Implications for their use as magnetic resonance contrast agents", Magnetic Resonance in Medicine 8: 180-190 (1988).*

* cited by examiner

*Primary Examiner* — Anand Desai
(74) *Attorney, Agent, or Firm* — Jackson IPG PLLC; Demian K. Jackson (57) ABSTRACT

A bonding method is provided for gold nanoparticles (GNPs). GNPs are bonded with diethylenetriamine pentaacetic acid (DTPA). GNPs have high bio-compatibility and high surface area. Hence, the present invention uses GNPs as carriers for diagnosing and treating cancer.

15 Claims, 10 Drawing Sheets

METHOD OF BONDING GOLD NANOPARTICLES WITH DIETHYLENETRIAMINE PENTAACETIC ACID

TECHNICAL FIELD OF THE INVENTION

The present invention relates a bonding method for gold nanoparticles (GNPs) with diethylenetriamine pentaacetic acid (DTPA); more particularly, relates to using GNPs as carriers with high bio-compatibility and high surface area for diagnosing and treating cancer.

DESCRIPTION OF THE RELATED ARTS

Biological technologies are used in many fields, like biochemistry.

A nanoparticle means a particle having a size of 1~100 nm. Its shape can be a ball, a column or a cube for different applications. Cancer diagnosis or treatment may use a nano material as a carrier for better drug effect, like liposome, micelles, GNPs, etc. [Liu, G., Swierczewska, M., Lee, S. and Chen, X., Functional Nanoparticles for Molecular Imaging Guided Gene Delivery. Nano Today. 2012, 5, 524-539] Nanoparticles have EPR effect in a living body, which means a nano material (<300 nm) may enter incomplete hemoendothelial cells to be gathered in a cancer tissue. However, small particles may be easily lost. Hence, nano materials can be used as drug carriers for cancer diagnosis or treatment.

Different GNPs show different colors. Red GNPs are 10~20 nm; purple ones, ~100 nm; and, black ones, more than 100 nm. For synthesizing GNPs, a solution of gold chloride ($HAuCl_4$ having $Au^{3+}$) is added with a reductant (e.g. sodium borohydride ($NaBH_4$)) for dissociating gold ions. Then, a stabilizer (e.g. thio-based peptide or protein) is added to be adhered on the GNPs for preventing gold ions from escaping. Or, sodium citrate ($C_6H_5Na_0O_7$) can be used as a reductant to be followed with a stabilizer. [Baptista, P., Pereira, E., Eaton, P., Doria, G., et al., Gold nanoparticles for the development of clinical diagnosis methods. Anal Bioanal Chem. 2008, 391, 943-950]

Various compounds can be bonded on the surface of GNPs, like, DNA, protein or drug. [Zhang, Y. F., Wang, J. C., Bian, D. Y., Zhang, X. and Zhang, Q., Targeted delivery of RGD-modified liposomes encapsulating both combretastatin A-4 and doxorubicin for tumor therapy: in vitro and in vivo studies. Eur J Pharm Biopharm. 2010, 74, 467-473; Shieh, M. J., Hsu, C. Y., Huang, L. Y., Chen, H. Y., et al., Reversal of doxorubicin-resistance by multifunctional nanoparticles in MCF-7/ADR cells. J Control Release. 2011, 152, 418-425; Krishna, A. D., Mandraju, R. K., Kishore, G. and Kondapi, A. K., An efficient targeted drug delivery through apotransferrin loaded nanoparticles. PLoS One. 2009, 4, e7240.] GNPs have good bio-compatibility and high surface area to be used in biological applications for enhancing drug effect on disease like cancer. [Zhang, Z., Jia, J., Lai, Y., Ma, Y., et al., Conjugating folic acid to gold nanoparticles through glutathione for targeting and detecting cancer cells. Bioorg Med Chem. 2010, 18, 5528-5534; Chithrani, D. B., Jelveh, S., Jalali, F., van Prooijen, M., et al., Gold nanoparticles as radiation sensitizers in cancer therapy. Radiat Res. 2010, 173, 719-728; Chanda, N., Kan, P., Watkinson, L. D., Shukla, R., et al., Radioactive gold nanoparticles in cancer therapy: therapeutic efficacy studies of GA-198AuNP nanoconstruct in prostate tumor-bearing mice. Nanomedicine. 2010, 6, 201-209; Lim, Z. Z., Li, J. E., Ng, C. T., Yung, L. Y. and Bay, B. H., Gold nanoparticles in cancer therapy. Acta Pharmacol Sin. 2011, 32, 983-990; Jain, S., Hirst, D. G. and O'Sullivan, J. M., Gold nanoparticles as novel agents for cancer therapy. Br J Radiol. 2012, 85, 101-113.]

Thio group can be reacted with the GNPs to form a stable ionic bond. For example, a prior art reveals albumin to stabilize GNPs for laser treatment. Yet, it is not found to use albumin as a bond between GNPs and diethylenetriamine pentaacetic acid (DTPA) for radiopharmacy. Hence, the prior arts do not fulfill all users' requests on actual use.

SUMMARY OF THE INVENTION

The main purpose of the present invention is to use GNPs as carriers with high bio-compatibility and high surface area for diagnosing and treating cancer.

To achieve the above purpose, the present invention is a method of bonding GNPs with DTPA, comprising steps of: (a) obtaining 1 mL of 0.1M of $HAuCl_4$ to be dissolved into 500 mL of ultrapure water; and adding 10 mL of $NaBH_4$ with stirring to form a solution of GNPs; (b) obtaining 1 mL of bovine serum albumin (BSA) with deionized water; adding 2 mL of the solution of GNPs to adhere BSA on surface of the GNPs; processing purification; and obtaining liquid phase of a phosphate buffer; and (c) obtaining 50 mg of BSA in 0.1M of a carbonate-bicarbonate buffer to be reacted with 1 mg of a DTPA to form a volume of 1 mL; processing a first purification; adding 2 mL of the solution of GNPs to be reacted; and obtaining liquid phase of a phosphate buffer. Accordingly, a novel method of bonding GNPs with DTPA is obtained.

BRIEF DESCRIPTIONS OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
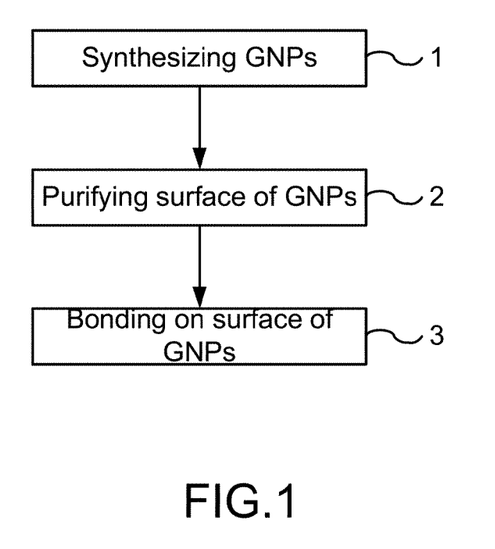
FIG. 1 is the view showing the preferred embodiment according to the present invention.
Figure 2:
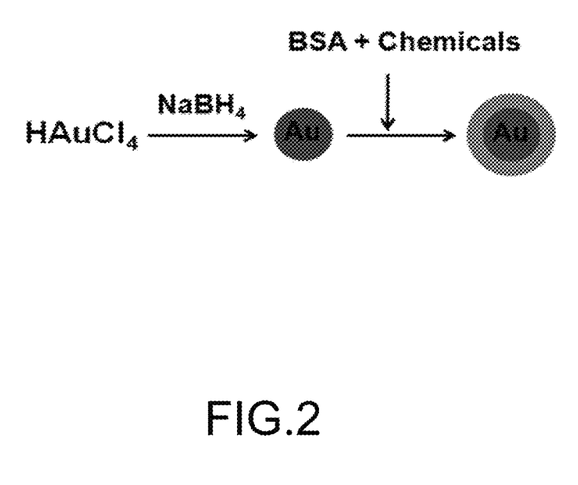
FIG. 2 is the view showing the step (a)

Please refer to FIG. 1 to FIG. 10, which are a view showing a preferred embodiment according to the present invention; views showing step (a) and step (b); a view showing purification of a solution of GNPs with G-25 columns; views showing full-spectrum analysis of GNPs and GNPs-BSA; a view showing a granular size analysis of GNPs; views showing a biotoxicity test of GNPs; and a view showing a bonding of GNPs to DTPA. As shown in the figures, the present invention is a method of bonding gold nanoparticles (GNPs) with diethylenetriamine pentaacetic acid (DTPA), comprising the following steps:

(a) Synthesizing GNPs 1: 1 mL of 0.1M of gold chloride (HAuCl$_4$) is dissolved into 500 mL of ultrapure water. Furthermore, 10 mL of sodium borohydride (NaBH$_4$) is slowly added with stirring so that solution color is changed from yellow to ruby red. After keeping stirring for 30 minutes (min), a solution of GNPs is obtained, where the GNPs in the solution have granular sizes of 10~20 nm.

Figure 3:
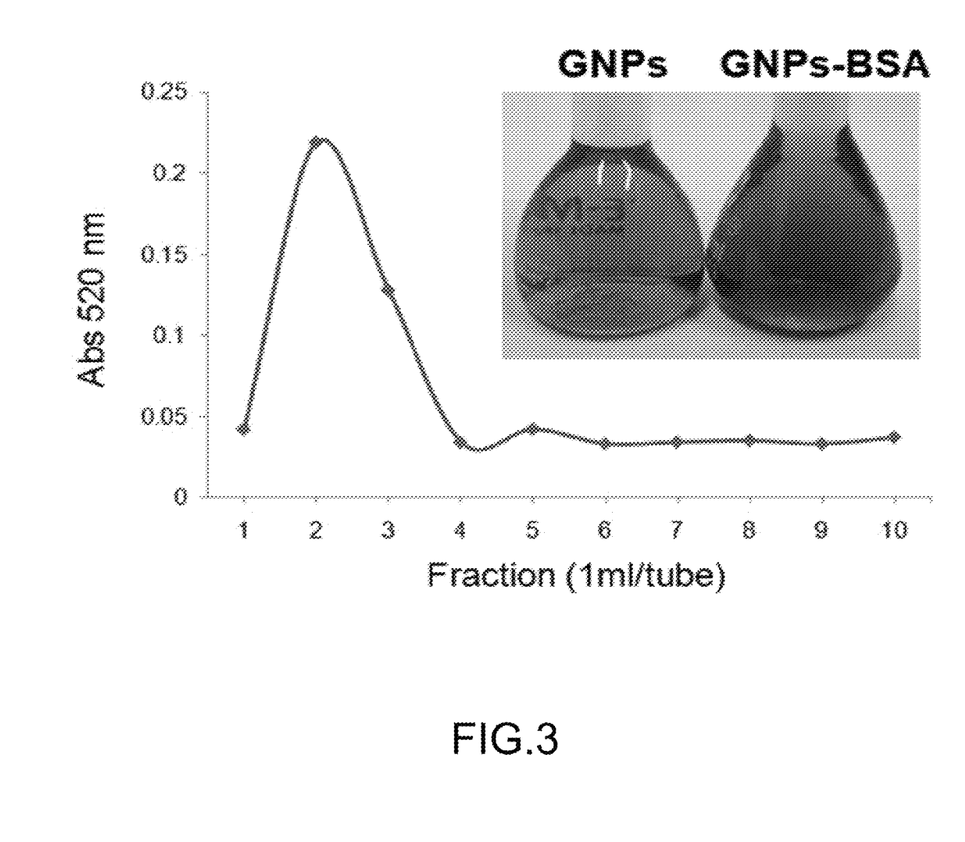
FIG. 3 is the view showing the step (b)
Figure 4:
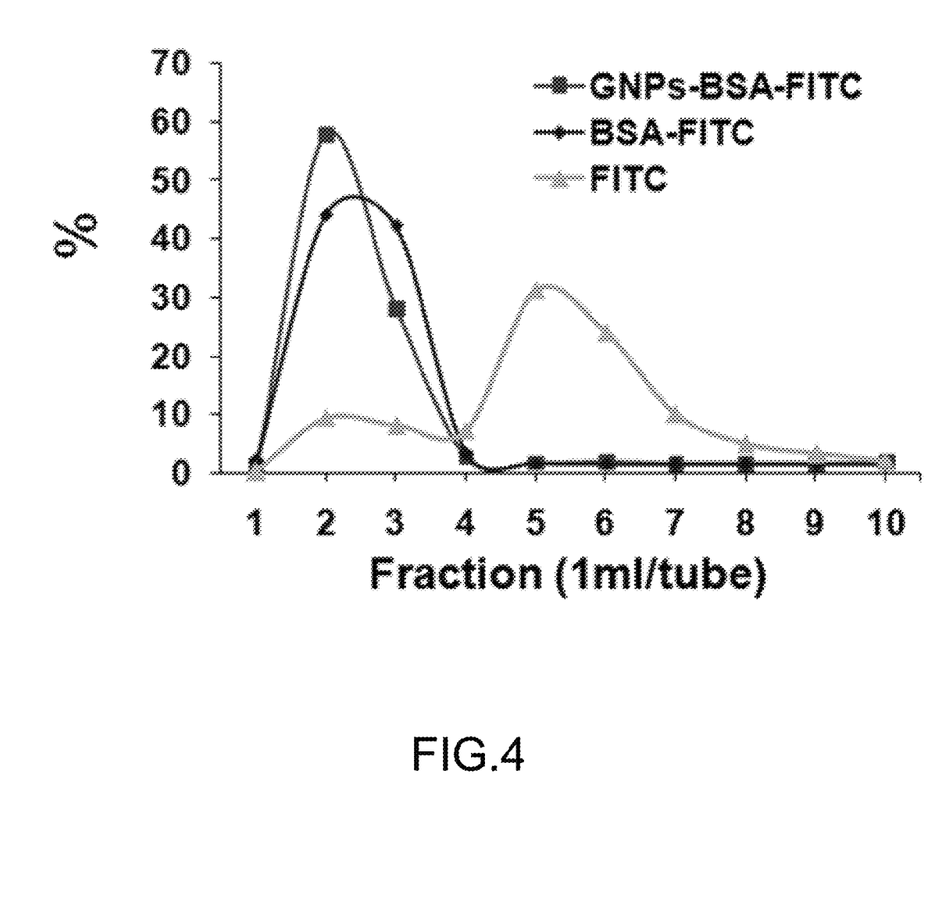
FIG. 4 is the view showing the purification of the solution of GNPs with the G-25 columns.

(b) Purifying surface of GNPs 2: A deionized water is used to make 1 mL of 50 mg/mL of bovine serum albumin (BSA). The BSA solution is added into 2 mL of the solution of GNPs with stirring for 1 hour (hr). Thus, BSA is adhered on surface of GNPs and the color is change from ruby red to purple. Then, G-25 columns are used for purification, where liquid phase is changed into a phosphate buffer.

Figure 10:
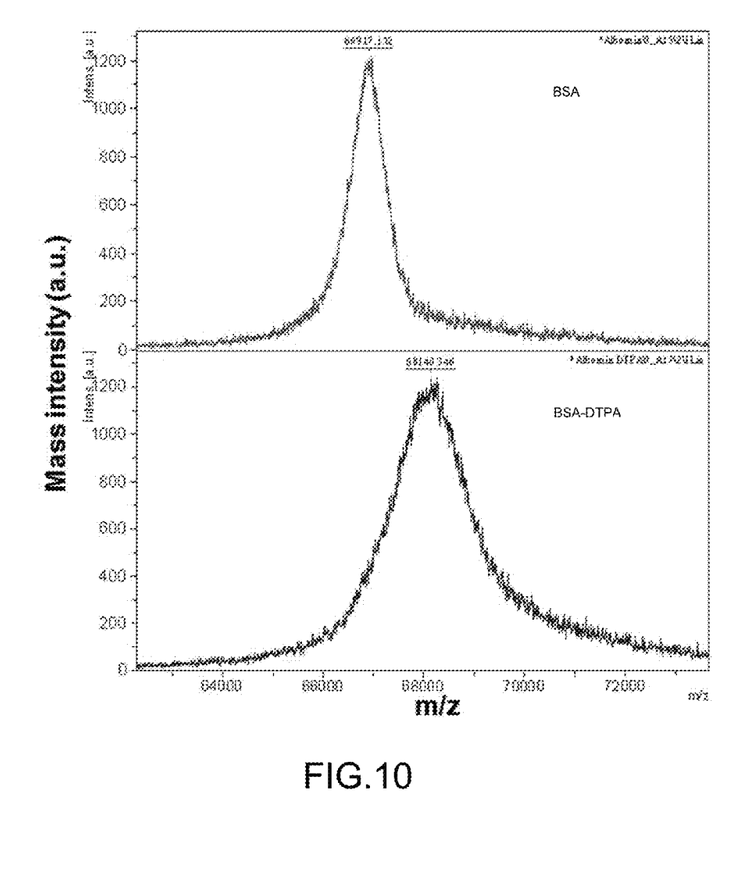
FIG. 10 is the view showing the bonding of the GNPs to DTPA.

(c) Bonding on surface of GNPs 3: 50 mg of BSA in 0.1M pH9.0 carbonate-bicarbonate buffer is reacted with 1 mg of DTPA for 2 hrs in a volume of 1 mL. Then, G-25 columns are used for purification (2~3 columns of purified product are collected with liquid phase of secondary water). Then, the purified product is added and reacted with 2 mL of the solution of GNPs for reaction at a room temperature for 2 hrs. Then, the final product is purified with G-25 columns again and liquid phase is changed into a phosphate buffer.

Figure 5:
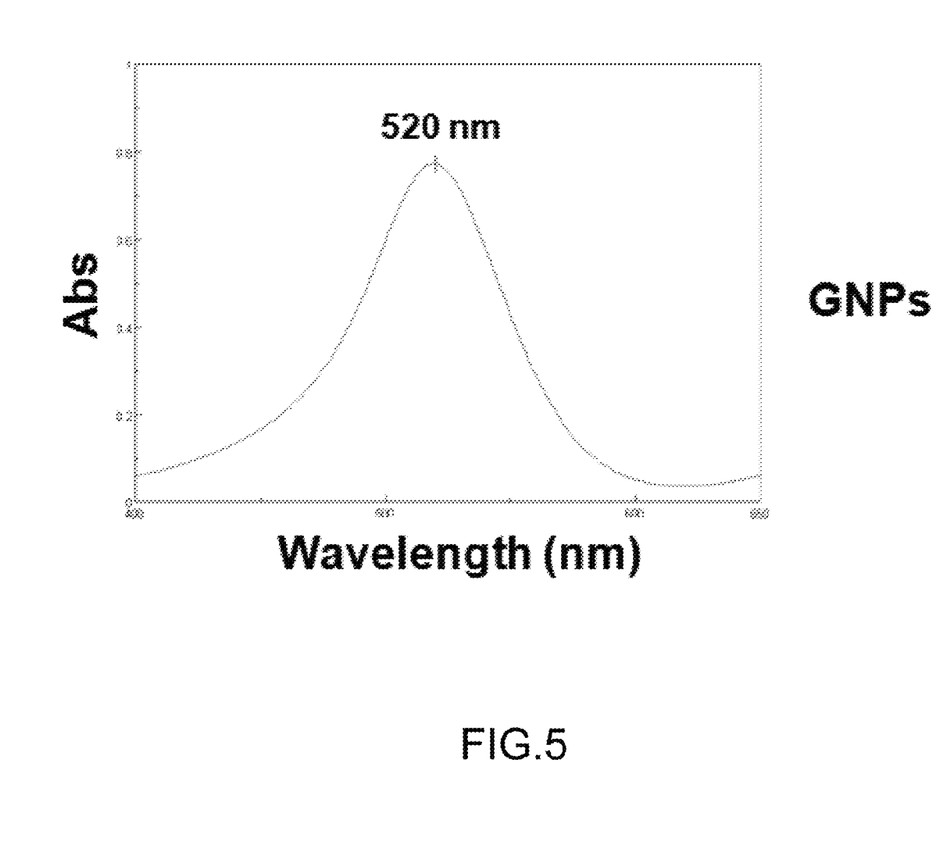
FIG. 5 is the view showing the full-spectrum analysis of the GNPs.
Figure 6:
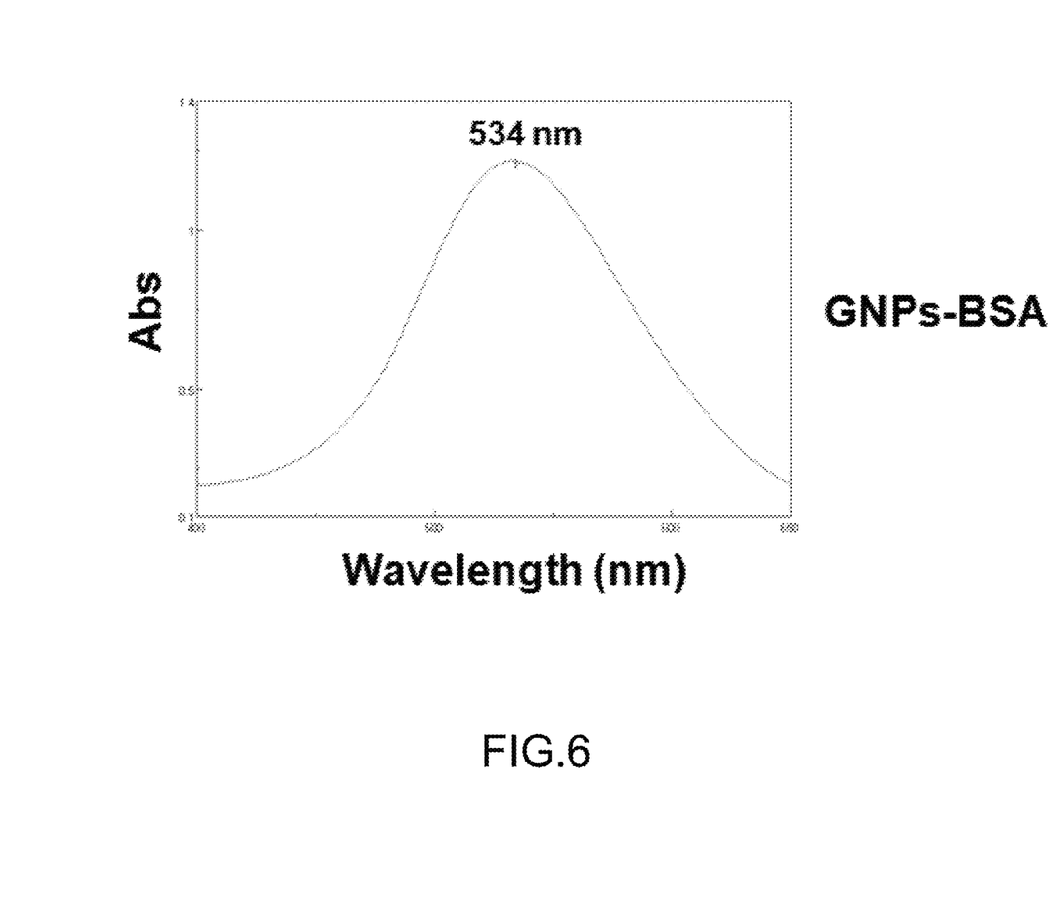
FIG. 6 is the view showing the full-spectrum analysis of the GNPs-BSA.
Figure 7:
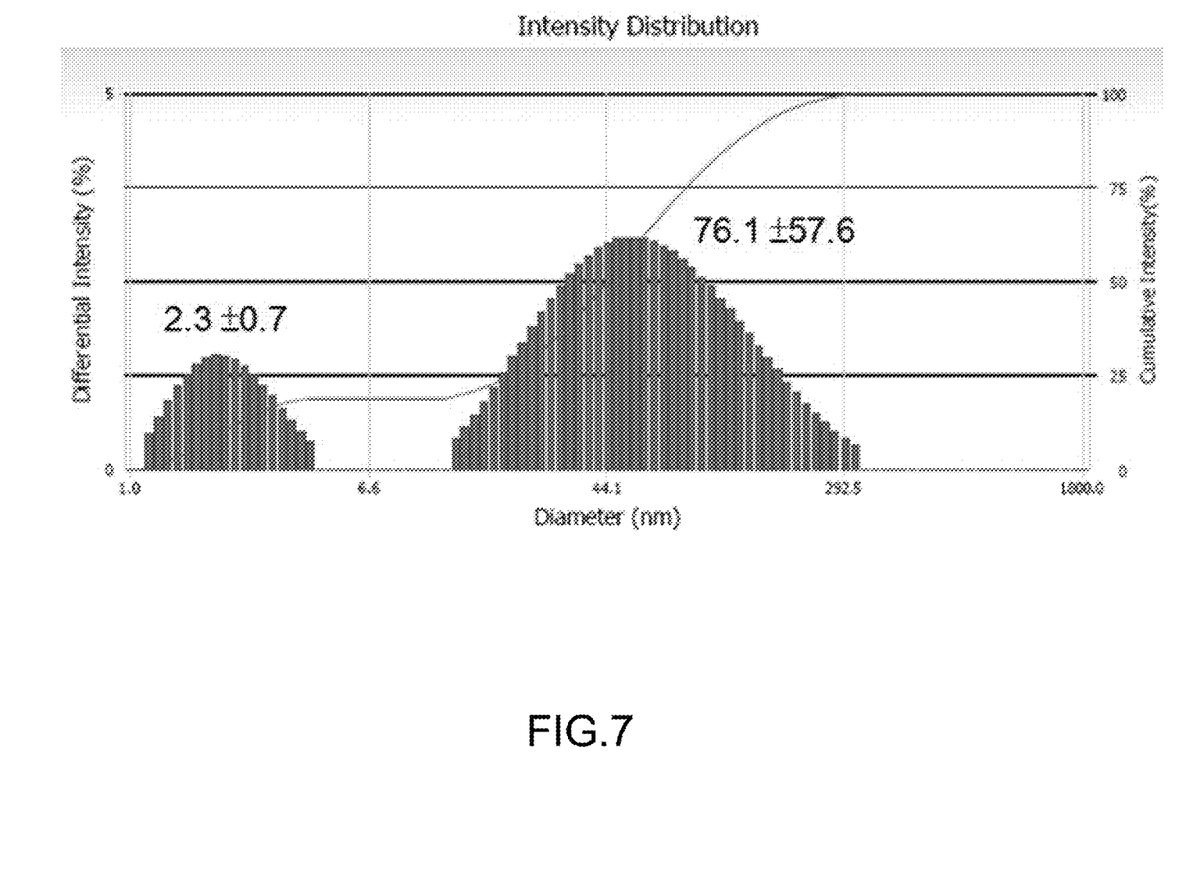
FIG. 7 is the view showing the granular size analysis of the GNPs.
Figure 8:
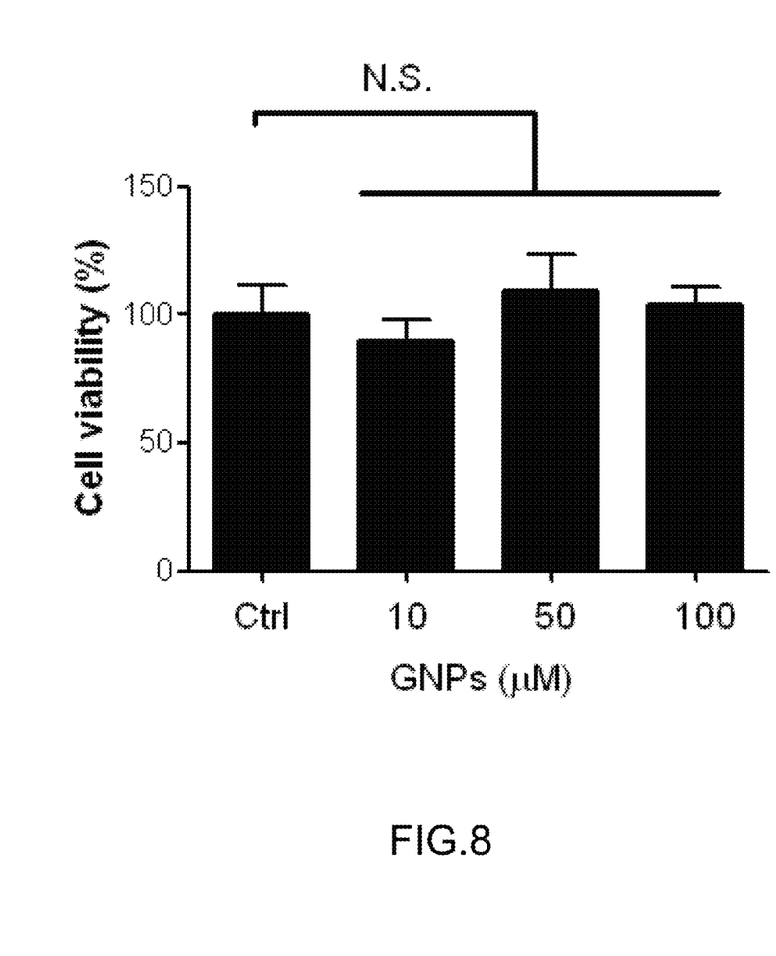
FIG. 8 and FIG. 9 are the views showing the biotoxicity test of the GNPs.
Figure 9:
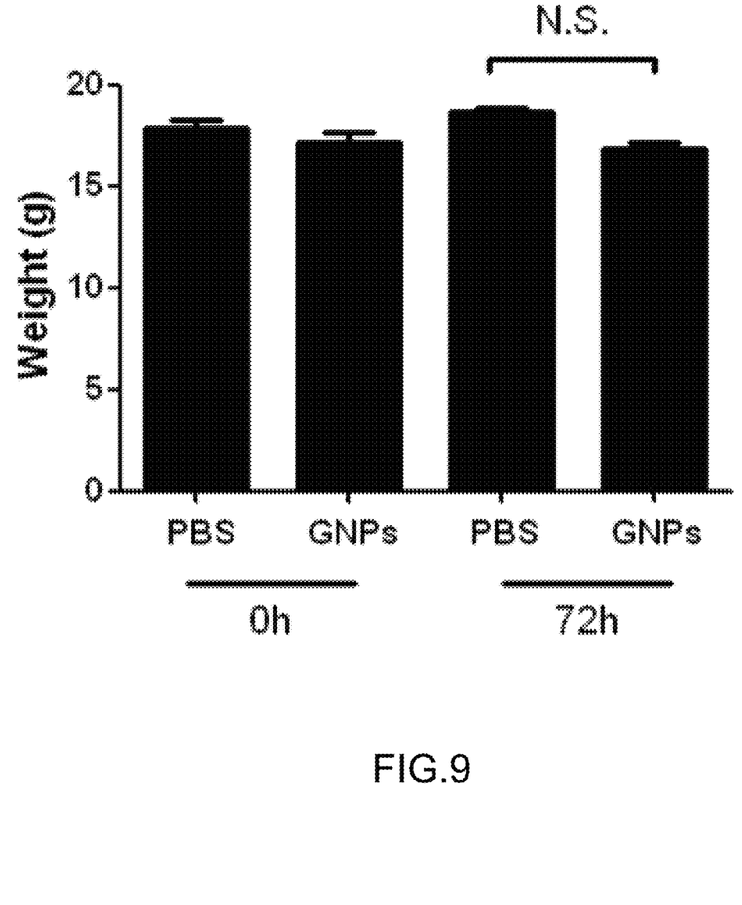

In FIG. 2 and FIG. 3, BSA is used as a stabilizer for GPNs-BSA, where solution color is changed into purple and is diluted from a G-25 column after purification. The GNPs which are not bonded with the stabilizer are bonded with resin and stayed in the G-25 columns (data not shown). In FIG. 5 and FIG. 6, the GNPs are processed through a full-spectrum analysis. The ruby-red GNPs have a wavelength of 520 nm and the GNPs-BSA (bonded with BSA) have a wavelength of 534 nm. It shows that BSA is adhered on surface of GNPs and makes the sizes of the GNPs bigger. Hence, the sizes of GNPs are found around 76 nm (FIG. 7).

Gold is an inert metal, which is not easily chemically reacted with other material, and is highly bio-compatible. The synthesized GNPs-BSA is cultured with cancer cell MKN45 under different densities for detecting cell numbers and activity through WST-1. As a result shown in FIG. 8, GNPs-BSA is smaller than 100 μM, which would not restrain growth of cell tissue. Besides, with GNPs-BSA injected into a rat, weight of the rat has no significant change within 72 hrs. As a result shown in FIG. 9, toxicity of GNPs-BSA is low and has a potential to be used as a drug carrier.

GNPs-BSA can be used as a bonding agent. After DTPA and BSA are reacted at a room temperature, a mass spectrometer is used for testing bonding efficiency. In FIG. 10, the molecular weight of BSA is 66.9 kDa; and, after bonding with DTPA, the molecular weight of BSA-DTPA is 68.1 kDa. Because the molecular weight of DTPA is 393 Da, a ratio of BSA to DTPA is 1:3.

To sum up, the present invention is a method of bonding GNPs with DTPA, where GNPs are used as carriers with high bio-compatibility and high surface area for diagnosing and treating cancer.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of bonding gold nanoparticles (GNPs) with diethylenetriamine pentaacetic acid (DTPA), comprising steps of:

(a) dissolving 1 mL±10% of 0.1M of gold chloride (HAuCl$_4$) in 500 mL±10% of ultrapure water; and adding 10 mL±10% of sodium borohydride (NaBH$_4$) with stirring to obtain a solution of GNPs;

(b) preparing 1 mL±10% of bovine serum albumin (BSA) solution with deionized water; adding the BSA solution to 2 mL±10% of said solution of GNPs with stirring to adhere BSA on surfaces of said GNPs; and purifying the mixed BSA and GNPs solutions to obtain a liquid phase of a phosphate buffer; and (c) reacting 50 mg±10% of BSA in 0.1M of a carbonate-bicarbonate buffer with 1 mg±10% of diethylenetriamine pentaacetic acid (DTPA) in solution with a volume of 1 mL; then processing a first purification to obtain an initially purified product; then adding the initially purified product to 2 mL of said solution of GNPs and reacting the mixture; and secondarily purifying the mixture again such that the liquid phase is changed into a phosphate buffer.

2. The method according to claim 1, wherein, in step (a), solution color is changed from yellow into ruby red.

3. The method according to claim 1, wherein, in step (a), a concentration of NaBH$_4$ is 6 mg/mL.

4. The method according to claim 1, wherein, in step (a), said GNPs have granular sizes of 10~20 nanometers (nm).

5. The method according to claim 1, wherein, in step (a), time of stirring is 30 minutes (min).

6. The method according to claim 1, wherein, in step (b), said BSA has a concentration of 50 mg/mL.

7. The method according to claim 1, wherein, in step (b), said stirring is performed at a room temperature for 1 hour (hr).

8. The method according to claim 1, wherein, in step (b), solution color is changed from ruby red into purple on adhering BSA on surface of said GNPs.

9. The method according to claim 1, wherein, in step (b), said purification is processed with G-25 columns.

10. The method according to claim 1, wherein, in step (c), said BSA is in solution with a concentration of 50 mg/mL.

11. The method according to claim 1, wherein, in step (c), said carbonate-bicarbonate buffer has a pH value of 9.0.

12. The method according to claim 1, wherein, in step (c), said DTPA is an isotope chelator.

13. The method according to claim 1, wherein, in step (c), reaction is processed for 2 hrs after adding said solution of GNPs.

14. The method according to claim 1, wherein, in step (c), said first and said second purifications are processed with G-25 columns.

15. The method according to claim 1, wherein, in step (c), said solution of GNPs is added to be reacted for 2 hrs at a room temperature after said first purification.

* * * * *